(12) United States Patent
Hammersberg

(10) Patent No.: US 11,922,716 B2
(45) Date of Patent: Mar. 5, 2024

(54) UNDER DISPLAY PASSIVE TERAHERTZ BIOMETRIC IMAGING DEVICE

(71) Applicant: Fingerprint Cards Anacatum IP AB, Gothenburg (SE)

(72) Inventor: Johan Hammersberg, Floda (SE)

(73) Assignee: Fingerprint Cards Anacatum IP AB, Gothenburg (SE)

( * ) Notice: Subject to any disclaimer, the term of this patent is extended or adjusted under 35 U.S.C. 154(b) by 0 days.

(21) Appl. No.: 17/909,370

(22) PCT Filed: Mar. 10, 2021

(86) PCT No.: PCT/SE2021/050210
§ 371 (c)(1),
(2) Date: Sep. 3, 2022

(87) PCT Pub. No.: WO2021/183032
PCT Pub. Date: Sep. 16, 2021

(65) Prior Publication Data
US 2023/0093461 A1 Mar. 23, 2023

(30) Foreign Application Priority Data
Mar. 13, 2020 (SE) .................................. 2050276-1

(51) Int. Cl.
*G06V 40/13* (2022.01)
*G01J 5/10* (2006.01)
(Continued)

(52) U.S. Cl.
CPC ............ *G06V 40/1318* (2022.01); *G01J 5/10* (2013.01); *G06V 40/1365* (2022.01);
(Continued)

(58) Field of Classification Search
CPC ................................ G06V 40/12; G06V 40/13
See application file for complete search history.

(56) References Cited

U.S. PATENT DOCUMENTS 7,351,974 B2 * 4/2008 Setlak ................ G06V 40/1318
250/341.1
2014/0326890 A1 11/2014 Debray et al.
(Continued)

FOREIGN PATENT DOCUMENTS

| CN | 109655841 A | 4/2019 |
| JP | 2005017644 A | 1/2005 |

(Continued)

OTHER PUBLICATIONS

Hillger, P. et al., "Terahertz Imaging and Sensing Applications With Silicon-Based Technologies," IEEE Transactions On Terahertz Science and Technology, vol. 9, No. 1, Jan. 2019, pp. 1-19.
(Continued)

*Primary Examiner* — Joseph R Haley
(74) *Attorney, Agent, or Firm* — RMCK Law Group, PLC

(57) ABSTRACT

The present invention relates to a passive terahertz biometric imaging device configured to be arranged under an at least partially transparent display panel and configured to capture a terahertz image of an object located on an opposite side of the transparent display panel, the terahertz biometric imaging device comprising: an image sensor comprising an antenna pixel array arranged to detect terahertz radiation produced by the object, for capturing a terahertz image of the object.

20 Claims, 10 Drawing Sheets

(51) Int. Cl.
  *G06V 40/12* (2022.01)
  *G06V 40/40* (2022.01)
  *G01J 5/00* (2022.01)

(52) U.S. Cl.
  CPC ...... *G06V 40/40* (2022.01); *G01J 2005/0077* (2013.01); *G01J 2005/106* (2013.01)

(56) References Cited

U.S. PATENT DOCUMENTS

| | | |
|---|---|---|
| 2016/0005154 A1 | 1/2016 | Meyers et al. |
| 2016/0084702 A1 | 3/2016 | Tomioka |
| 2017/0316487 A1 | 11/2017 | Mazed |
| 2019/0318146 A1 | 10/2019 | Trichopoulos et al. |
| 2019/0393374 A1* | 12/2019 | Rämer ............... H01Q 9/28 |
| 2020/0049620 A1 | 2/2020 | Zheng et al. |
| 2020/0133434 A1* | 4/2020 | Lawrence ........... G06F 3/04166 |
| 2020/0285345 A1* | 9/2020 | Xiang ................. G06F 3/0421 |
| 2020/0411599 A1* | 12/2020 | Yang ................. G06V 40/1306 |
| 2021/0150178 A1* | 5/2021 | Wang ................ G06V 40/1318 |

FOREIGN PATENT DOCUMENTS

| | | |
|---|---|---|
| WO | 2006088802 A2 | 8/2006 |
| WO | 2012078043 A1 | 6/2012 |
| WO | 2016114649 A1 | 7/2016 |
| WO | 2017093514 A1 | 6/2017 |
| WO | 2017216745 A1 | 12/2017 |
| WO | 2019049035 A1 | 3/2019 |
| WO | 2019125271 A1 | 6/2019 |

OTHER PUBLICATIONS

Hillger, P. et al., "A 128-Pixel System-on-a-Chip for Real-Time Super-Resolution Terahertz Near-Field Imaging," EEE Journal of Solid-State Circuits, vol. 53, No. 12, Dec. 2018, pp. 3599-3612.
Hillger, P. et al., "A Solid-State 0.56 THz Near-Field Array for μM-Scale Surface Imaging," IEEE, Sep. 2018, 3 pages.
PCT International Search Report and Written Opinion dated May 11, 2021 for International Application No. PCT/SE2021/050209, 11 pages.
PCT International Search Report and Written Opinion dated May 11, 2021 for International Application No. PCT/SE2021/050210, 12 pages.
PCT International Search Report and Written Opinion dated May 11, 2021 for International Application No. PCT/SE2021/050211, 13 pages.
An, B.W. et al., "Transparent And Flexible Fingerprint Sensor Array With Multiplexed Detection Of Tactile Pressure And Skin Temperature," Nature Communications, vol. 9, No. 1, Jul. 2018, 10 pages.
Extended European Search Report dated Jul. 5, 2023 for EP Application No. 21768742.5, 11 pages.
Extended European Search Report dated Jun. 27, 2023 for EP Application No. 21768586.6, 9 pages.
Vicarelli, L. et al., "Graphene Field-Effect Transistors As Room-Temperature Terahertz Detectors," Nature Materials, vol. 11, No. 10, Oct. 2012, 7 pages.
Yang, X. et al., "A Flexible Graphene Terahertz Detector," Applied Physics Letters, American Institute of Physics, vol. 111, No. 2, Jul. 2017, pp. 021102-1 -021102-4.
Yang, X. et al., "Supplementary Material: A Flexible Graphene Terahertz Detector," Applied Physics Letters, American Institute of Physics, vol. 111, No. 2, Jul. 2017, 3 pages.
Yang, X., "Graphene FET Terahertz Detectors on Flexible Substrates," Thesis, Chalmers University of Technology, Oct. 2017, https://publications.lib.chalmers.se/records/fullext/252774/252774.pdf, 65 pages.

* cited by examiner

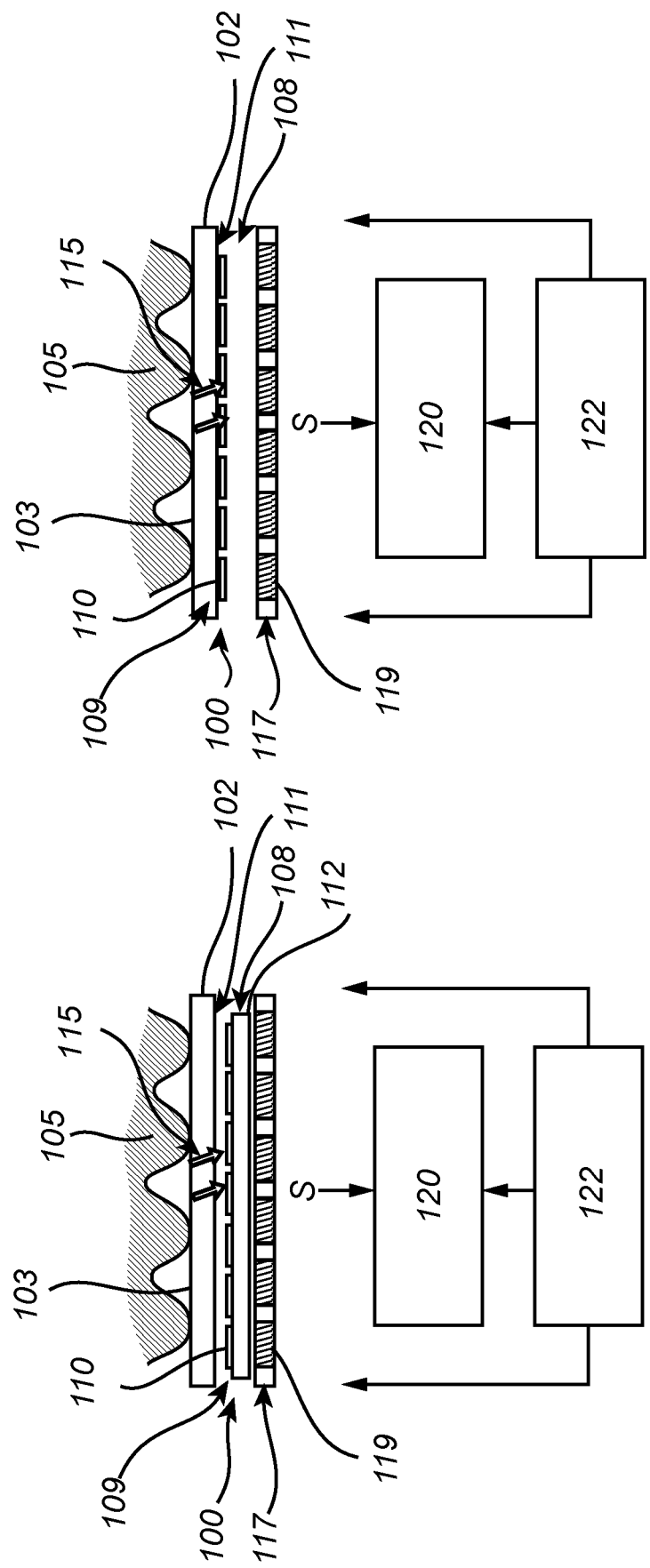

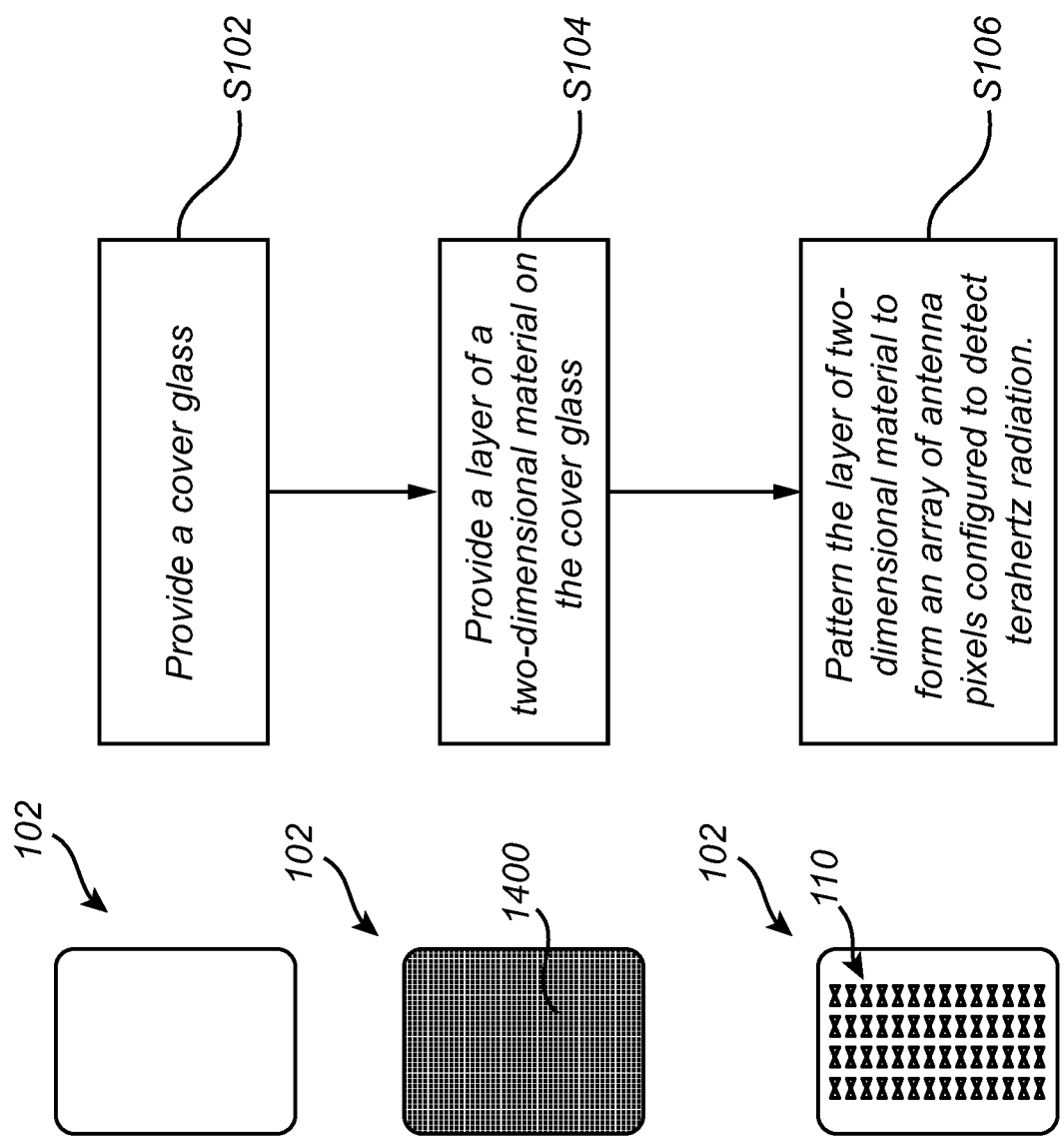

UNDER DISPLAY PASSIVE TERAHERTZ BIOMETRIC IMAGING DEVICE

CROSS-REFERENCE TO RELATED APPLICATIONS

This application is a 371 U.S. National Stage of International Application No. PCT/SE2021/050210, filed Mar. 10, 2021, which claims priority to Swedish Patent Application No. 2050276-1, filed Mar. 13, 2020. The disclosures of each of the above applications are incorporated herein by reference in their entirety.

FIELD OF THE INVENTION

The present invention relates to a passive terahertz biometric imaging device configured to be arranged under an at least partially transparent display panel. The present invention further relates to an electronic device comprising a passive terahertz biometric imaging device.

BACKGROUND OF THE INVENTION

Biometric systems are widely used as means for increasing the convenience and security of personal electronic devices, such as mobile phones etc. Fingerprint sensing systems, in particular, are now included in a large proportion of all newly released consumer electronic devices, such as mobile phones.

Optical fingerprint sensors have been known for some time and may be a feasible alternative to e.g. capacitive fingerprint sensors in certain applications. Optical fingerprint sensors may for example be based on the pinhole imaging principle and/or may employ micro-channels, i.e. collimators or microlenses to focus incoming light onto an image sensor. Optical fingerprint sensors have also proven to be suitable for arrangement under the display of electronic devices. However, many optical fingerprint sensors have turned out to be easily spoofed using even simple 2-dimensional images as fake fingerprints.

Accordingly, there is an interest in providing in-display fingerprint sensors with improved security against spoofs and fake biometric objects, to thereby prevent un-authorized users from gaining access to protected devices or systems.

SUMMARY

In view of the above-mentioned and other drawbacks of the prior art, it is an object of the present invention to provide an under-display biometric imaging device with improved ability to detect spoofs. In particular, the present invention relates to a passive terahertz biometric imaging device that operates in a terahertz range to capture an image of the object without the need for assisting illumination of the object.

According to a first aspect of the invention, there is provided a passive terahertz biometric imaging device configured to be arranged under an at least partially transparent display panel and configured to capture a terahertz image of an object located on an opposite side of the transparent display panel.

The passive terahertz biometric imaging device comprises an image sensor comprising an antenna pixel array arranged to detect terahertz radiation produced by the object, for capturing an image of the object. The image is advantageously a terahertz image.

The present invention is based on the realization that imaging at millimeter and sub-millimeter wavelengths, e.g. at frequencies in the "terahertz gap", provides for increasing the ability to detect structures under the outermost tissue layer of a fingerprint. In other words, sub-dermal layers of the fingerprint may be detected. It was realized that the wavelength in the terahertz gap is long enough to be detected using e.g. RF circuit design but also low enough to be considered as light when it comes to beam shaping optics that may be implemented in some embodiments. Further, the photon energy is low enough so that the photons are not absorbed in most materials, i.e. the penetration of the radiation may be e.g. up to 0.2 mm, into the skin, increasing the probability to detect fingerprint spoofs.

In addition, the present invention is based on the realization to passively detect the terahertz radiation produced by the object to in this way capture a terahertz biometric image. This provides for eliminating the need for a source that is fast enough to produce sufficient power at frequencies covering the terahertz frequencies, preferably in the terahertz gap discussed above. Further, by eliminating the source, a more compact biometric imaging device is obtained which is less complicated to mount under a display panel of an electronic device.

Still further, the elimination of the source means that fewer parts are needed for the biometric imaging device, thereby opening for more possibilities for mounting of the image sensor.

Still further, by means of the claimed invention, it may be possible to detect a fingerprint without requiring direct contact between the skin and the image sensor, and this ability is improved by the penetration of the radiation, thereby providing improved performance for biometric imaging devices for under-display arrangement compared to optical sensors operating in the visible range of light.

Terahertz radiation is herein preferably meant to include a range of radiation frequencies that are below the frequency of infrared light and above the frequency of microwaves, e.g. the range of terahertz radiation is herein meant to be about 100 GHz to about 10 THz.

The outer surface of the display panel under which the biometric imaging device is arranged may also be referred to as a sensing surface. The operating principle of the described biometric imaging device is that radiation produced by a finger placed on the sensing surface, is received by the antennas in the antenna pixel array which produce sensing signals indicative of the detected terahertz radiation. By combining the signals from all the antenna pixels, an image representing the fingerprint can be formed and subsequent biometric verification can be performed. The signals from each antenna pixel may be read in an e.g. column by column or row by row wise manner.

The antenna may be e.g. a dipole antenna e.g. employing a bow tie antenna configuration. A bow tie antenna typically employs an at least partly circular geometry which advantageously provides a more polarization independent antenna compared to dipole antennas employing more straight geometries. Thereby, using a bow tie antenna provides for increasing the signal strength of detected terahertz radiation. Antennas having higher numbers of poles are also conceivable.

Preferably, an antenna pixel may operate as a power detector, which acts as a sensor to detect the terahertz radiation produced by the object and to provide a DC signal, which level depends on the power of the detected terahertz radiation. In other words, the antenna pixel may be adapted to sense the incoming terahertz radiation and to output a low frequency signal or a DC voltage level or a DC current level that is based on the power of the detected incoming terahertz radiation. Thus, in embodiments, a level of a DC voltage or current output from an antenna pixel may be based on the power of the detected terahertz radiation.

Accordingly, by the provision of the antenna pixel as a power detector, a compact antenna pixel is obtained that allows for simple read-out since the signal output is already, on chip, adapted for an ADC to receive without requiring additional AC-to-DC conversion circuits. Thus, the antenna pixels comprise both the antenna itself for collecting the terahertz radiation, and a frequency converting element for converting the detected terahertz signal to a signal detectable by e.g. an ADC. The inventors thus realized an array of such compact power detectors for image capturing in the terahertz range for under display biometric applications where space is often limited.

The image sensor may thus include an array of power detectors arranged to detect terahertz radiation produced by the object, and to provide a low frequency signal output or a DC signal output.

Each of the antenna pixels may comprise a power detector including an antenna structure, the power detector is configured to convert a terahertz signal indicative of a detected terahertz radiation to a signal at a lower frequency than the frequency of the terahertz radiation, or to a DC signal.

Hereby, the image sensor may advantageously include an on-chip power detector that provides, as mentioned above, a measurable signal at a suitable frequency for an analogue-to-digital converter to read as input. The low frequency signal or DC signal from each antenna pixel are the output signals that are read for constructing a terahertz image. The power detector may hereby be an on-chip transistor structure electrically connected to the antenna of the pixel. Preferably, the antenna structure is part of the transistor structure.

The transistor structure and the antenna structure may be made in a single component. Thus, the pixel itself may comprise both the antenna and the transistor for rectifying the detecting signal.

The antenna pixel array may comprise a two-dimensional material. In other words, the antenna pixel array may be made from a two-dimensional material. A two-dimensional material generally only includes one or a few atom layers.

In embodiments, the antenna pixel array comprises graphene. Thus, the antenna pixel array may be made from graphene. Graphene is an example two-dimensional material and comprises one or a few layers of carbon atoms. Further, graphene is particularly suitable for the antenna structures and/or the power detector since graphene has high electrical mobility which means it allows for fast operation of a transistor structure made from graphene. Such transistors may be a graphene field effect transistor. Further, the electrical properties of graphene enable for modulating the electrical conductivity in a gate of a graphene structure which advantageously enables for frequency conversion for simple read-out as described above. Other two-dimensional materials may also be conceivable for embodiments herein.

Further, graphene is a two-dimensional material that is flexible or bendable when arranged on a flexible or bendable substrate which provides mounting advantages for under-display arrangements, in particular when the display panel is curved.

Contrary to bulk semiconductor transistors, graphene is a two-dimensional material and provides improved sensitivity compared to the conventional bulk transistors. For example, the gate, drain and source structures of a graphene FET transistor may serve as antenna, whereby the flow of current from source to drain is affected by terahertz radiation that impedes on the gate/antenna.

In addition, using graphene for the antenna pixel enables for an at least nearly optically transparent antenna pixel array. The advantageously allows for nearly arbitrary mounting location of the image sensor in the stack under the display panel, since it will not visually obstruct the appearance of the display.

Although graphene is an advantageous alternative for embodiments herein, other two-dimensional materials are also conceivable, such as e.g. silicene, germanene, and phosphorene but also TMDs as i.e., MoS2, WSe2, etc.

The image sensor may be operative to detect terahertz radiation in a frequency range excluding the range of visible light. The range of visible light is in the range of about 400 nm to 700 nm and is the visible range for humans. The image sensor thus comprises antennas that are designed to couple to the terahertz frequencies of radiation. The image sensor may be operative at frequencies in the terahertz range, e.g. 10 GHz to 100 THz.

Preferably, the image sensor may be operative in the frequency range 10 GHz to 100 THz, preferably, 100 GHz to 50 THz, more preferably 300 GHz to 30 THz, more preferably 100 GHz to 10 THz, more preferably 300 GHz to 10 THz.

The antennas are micro-sized antennas, e.g. in the range of a few micrometer, to thereby fit a large number of antennas in the antenna pixel array. Further, the dimension and design of the antenna and associated circuitry provides for tuning the antenna pixel for a specific terahertz frequency range. The size of an antenna pixel may be in the range of about 15 micrometers to about 150 micrometer.

In one embodiment, the image sensor may be attached to the display panel. This provides for a small stack-height for the biometric imaging device. For example, the image sensor may be stacked with the display panel meaning that the image sensor is arranged in parallel with the display panel. Thus, a surface of the image sensor, preferably where the array of antenna pixels is arranged, is attached to a back side of the display panel. The back side of the display panel is opposite the sensing surface of the display panel where a finger is intended to touch or approach for imaging.

In one embodiment, the image sensor may comprise a substrate supporting the antenna pixel array. The substrate may be made from a flexible material. This advantageously provides for improved integration under displays of different shapes. For example, with a flexible substrate, the image sensor may be conformally shaped with a curved display panel.

Advantageously, the image sensor may be laminated directly on the display panel. The image sensor may for example be glued onto the back side of the display panel.

In one embodiment, the image sensor may be at least partly transparent. This further enables placing the image sensor close to the display panel since it will not substantially obstruct the visual appearance of the display panel.

In some implementations, the display panel stack may comprise a display element including color controllable array of light sources. Various types of displays can be used in accordance with embodiments. For example, display elements based on OLED, u-LED with any type of tri-stimulus emission like RGB, CMY or others.

In such implementations, the image sensor may be arranged between a display element comprising the color controllable array of light sources and a top cover glass of the display panel. Thus, the image sensor may be stacked between the color controllable array of light sources and the top cover glass. This is especially suitable when the antenna pixels comprise two-dimensional material.

In some embodiments, the image sensor may be arranged under a display element comprising an array of color controllable light sources. Accordingly, as seen from the outer surface of the transparent display panel, the image sensor is arranged under a top cover glass and the display element.

In embodiments, the image sensor may comprise a substrate supporting the antenna pixel array, wherein the substrate may be made from an at least partly transparent material. This advantageously allows the image sensor to be placed in any stacking position of the display stack, from top-to bottom.

In some embodiments, an array of terahertz radiation redirecting elements arranged between the display panel and the image sensor, wherein each terahertz radiation redirecting element is configured to redirect terahertz radiation onto the antenna pixel array. Each terahertz radiation redirecting element may be configured to redirect terahertz radiation onto a sub-array of antenna pixels or onto a single antenna pixel. The introduction of terahertz radiation redirecting elements improves the integration of a layered biometric imaging device by enabling efficient guiding of the terahertz radiation from the biometric object to the antenna pixel array.

Different types of terahertz radiation redirecting elements are conceivable. In one advantageous embodiment, the array of terahertz radiation redirecting elements may be an array of microlenses, wherein each microlens is configured to redirect terahertz radiation onto a subarray of pixels or into a single pixel in the antenna pixel array. Microlenses provide an advantageous way to redirect terahertz radiation onto the antenna pixel array.

The array of microlenses may be arranged on a transparent substrate arranged to cover the image sensor. This simplifies the manufacturing of the passive terahertz biometric imaging device since the microlenses may all be manufactured on the same transparent substrate. Further, having all the microlenses arranged on a single substrate facilitates the task of getting the microlenses in a single plane.

An opaque layer may be arranged to cover an upper surface of the transparent substrate. The opaque layer further comprises a plurality of separate openings, wherein each of the microlenses is located in a respective opening in the opaque layer. This advantageously ensures that limited stray terahertz radiation is detected by the image sensor, i.e. it prevents terahertz radiation reaching the image sensor that has not passed through a microlens.

In a further embodiment, the array of terahertz radiation redirecting elements may be an array of vertical waveguides wherein each vertical waveguide is configured to redirect terahertz radiation onto an antenna pixel in the antenna pixel array. Several types of vertical waveguides are conceivable and within the scope of the present invention. For example, hollow metallic waveguides, coaxial waveguides, only mentioned as examples.

With terahertz radiation redirecting elements, the terahertz radiation produced by the object is received by terahertz radiation redirecting elements and subsequently redirected onto a corresponding subarray of antennas or a single antenna in the antenna pixel array. In case of a subarray, an image of a portion of a finger can be captured for each subarray. As mentioned above, by combining the images from all the terahertz radiation redirecting elements, an image representing the fingerprint can be formed and subsequent biometric verification can be performed.

The inclusion of terahertz radiation redirecting elements is advantageous for the passive operation of the biometric imaging device since they enable for focusing or directing the radiation produced by the object towards or even directly to the antenna pixel array, or even to a single antenna pixel.

Advantageously, embodiments of the herein provided passive terahertz biometric imaging device is configured to capture a terahertz image of an object based on terahertz radiation produced by the object without assisting terahertz radiation that illuminates the object.

According to a second aspect of the invention, there is provided an electronic device comprising: an at least partly transparent display panel, the passive terahertz biometric imaging device according to any one of the herein described embodiments, and processing circuitry configured to: receive a signal from the passive terahertz biometric imaging device indicative of a biometric object touching the transparent display panel, and perform a biometric authentication procedure based on the detected biometric object.

Biometric authentication procedures such as fingerprint authentication procedures are known per se, and generally includes to compare features of a verification representation constructed based on an acquired fingerprint image, with features of an enrollment representation constructed during enrollment of a user. If a match with sufficiently high score is found, the user is successfully authenticated.

The biometric object may be a finger, whereby the signal is indicative of a fingerprint of the finger.

The electronic device is a mobile device, such as a mobile phone (e.g. Smart Phone), a tablet, a laptop, or any other portable device suitable for an under-display biometric imaging device.

The display panel may include a display element that may for example be based on OLED, LCD, µLED and similar technologies. Thereby, in-display passive biometric terahertz imaging is enabled.

In embodiments, the image sensor is configured to cover at least a quarter of the display panel area.

In embodiments, the image sensor is configured to cover at least half of the display panel area.

In embodiments, the image sensor is configured to covers substantially the entire display panel area.

Further effects and features of the second aspect of the invention are largely analogous to those described above in connection with the first aspect of the invention.

According to a third aspect of the invention, there is provided a method of manufacturing an image sensor for a terahertz biometric imaging device, the method comprising: providing a cover glass configured to cover a display for an electronic device; providing a layer of a two-dimensional material on the display panel; patterning the layer of two-dimensional material to form an array of antenna pixels configured to detect terahertz radiation.

The two-dimensional material may be deposited directly on the cover glass or the two-dimensional material may be transferred from a substrate onto the cover glass. Other materials needed for the antenna pixels such as metal lines and dielectric materials may be deposited directly on the cover glass using known microfabrication techniques.

Further effects and features of the third aspect of the invention are largely analogous to those described above in connection with the first aspect and the second aspect of the invention.

Alternatively, the method is for manufacturing a combined cover glass and image sensor for a passive terahertz biometric imaging device Further features of, and advantages with, the present invention will become apparent when studying the appended claims and the following description. The skilled person realize that different features of the present invention may be combined to create embodiments other than those described in the following, without departing from the scope of the present invention.

BRIEF DESCRIPTION OF THE DRAWINGS

These and other aspects of the present invention will now be described in more detail, with reference to the appended drawings showing an example embodiment of the invention, wherein:

FIG. 6A schematically illustrates a passive terahertz biometric imaging device according to an embodiment of the invention;

FIG. 6B schematically illustrates a passive terahertz biometric imaging device according to an embodiment of the invention;

FIG. 13 is a flow-chart of method steps for manufacturing an image sensor for a terahertz biometric imaging device according to embodiments of the invention.

DETAILED DESCRIPTION OF EXAMPLE EMBODIMENTS

In the present detailed description, various embodiments of the passive terahertz biometric imaging device according to the present invention are mainly described with reference to a passive terahertz biometric imaging device arranged under a display panel. However, it should be noted that the described imaging device also may be used in other biometric imaging applications such as located under a cover glass or the like.

Figure 1:
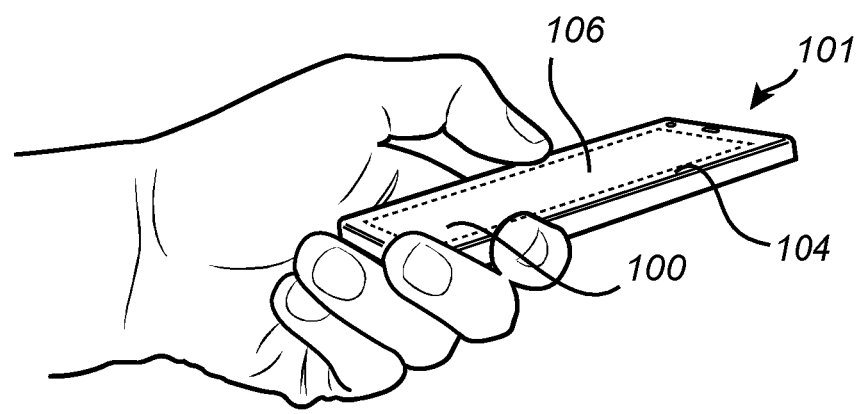
FIG. 1 schematically illustrates an example of an electronic device according to embodiments of the invention.

Turning now to the drawings and in particular to FIG. 1, there is schematically illustrated an example of an electronic device configured to apply the concept according to the present disclosure, in the form of a mobile device 101 with an integrated in-display passive terahertz biometric imaging device 100 and a display panel 104 with a touch screen interface 106. The passive terahertz biometric imaging device 100 may, for example, be used for unlocking the mobile device 101 and/or for authorizing transactions carried out using the mobile device 101, etc.

The passive terahertz biometric imaging device 100 is here shown to be smaller than the display panel 104, but still relatively large, e.g. a large area implementation. In another advantageous implementation the passive terahertz biometric imaging device 100 may be the same size as the display panel 104, i.e. a full display solution. Thus, in such case the user may place his/her finger anywhere on the display panel for biometric authentication. The passive terahertz biometric imaging device 100 may in other possible implementations be smaller than the depicted biometric imaging device, such as providing a hot-zone implementation.

Preferably and as is apparent for the skilled person, the mobile device 100 shown in FIG. 1 further comprises a first antenna for WLAN/Wi-Fi communication, a second antenna for telecommunication communication, a microphone, a speaker, and a phone control unit. Further hardware elements are of course possibly comprised with the mobile device.

It should furthermore be noted that the invention may be applicable in relation to any other type of electronic devices comprising transparent display panels, such as a laptop, a tablet computer, etc.

Figure 2:
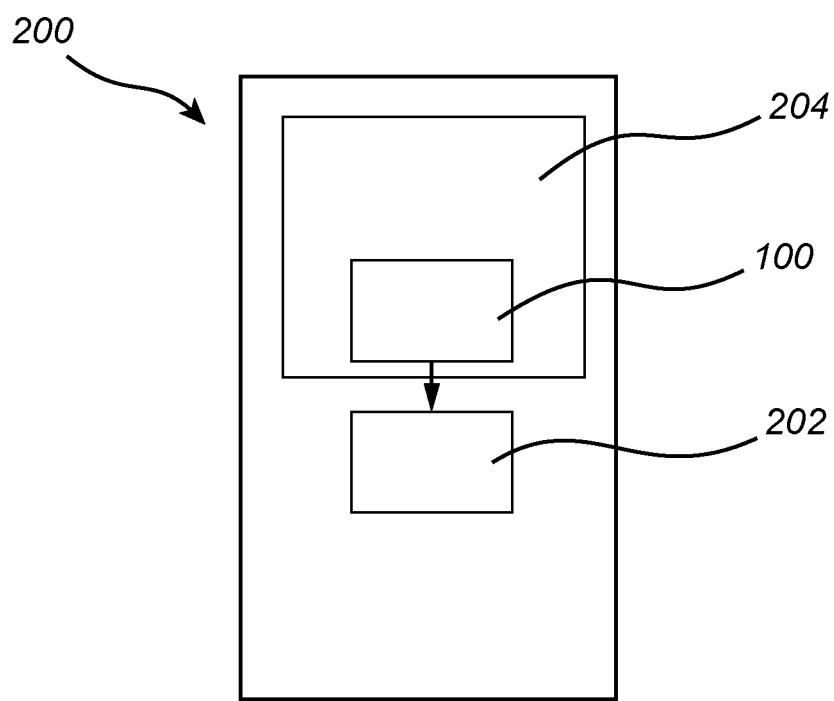
FIG. 2 is a schematic box diagram of an electronic device according to embodiments of the invention.

FIG. 2 is a schematic box diagram of an electronic device according to embodiments of the invention. The electronic device 200 comprises a transparent display panel 204 and a passive terahertz biometric imaging device 100 conceptually illustrated to be arranged under the transparent display panel 204 according to embodiments of the invention. Furthermore, the electronic device 200 comprises processing circuitry such as control unit 202. The control unit 202 may be stand-alone control unit of the electronic device 202, e.g. a device controller. Alternatively, the control unit 202 may be comprised in the passive terahertz biometric imaging device 100.

The control unit 202 is configured to receive a signal indicative of a detected object from the biometric imaging device 100. The received signal may comprise image data.

Based on the received signal the control unit 202 is configured to detect a fingerprint, or other biometric objects, and, based on the detected fingerprint the control unit 202 is configured to perform a biometric authentication procedure e.g. a fingerprint authentication procedure. Such biometric or fingerprint authentication procedures are considered per se known to the skilled person and will not be described further herein.

Figure 3A:
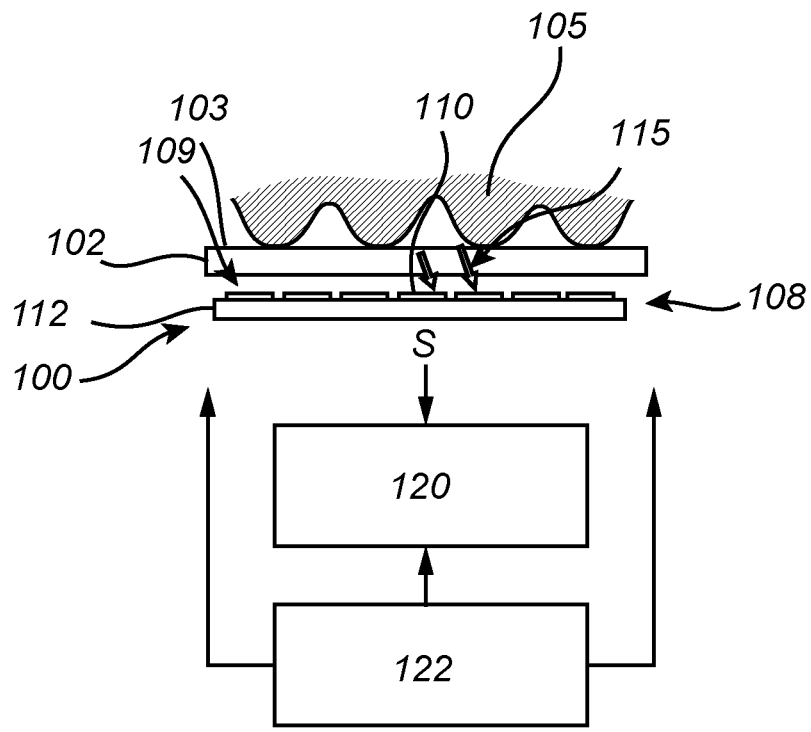
FIG. 3A schematically illustrates a passive terahertz biometric imaging device according to an embodiment of the invention.

FIG. 3A schematically illustrates a passive terahertz biometric imaging device 100 according to an embodiment of the invention. The passive terahertz biometric imaging device 100 is here arranged under an at least partially transparent display panel 102. However, the biometric imaging device 100 may be arranged under any cover structure which is sufficiently transparent, as long as the image sensor receives a sufficient amount of terahertz radiation to capture a terahertz image of a biometric object in contact with or nearby the outer surface of the cover structure, such as a fingerprint or a palmprint. In the following, a passive terahertz biometric imaging device 100 configured to capture an image of a finger 105 in contact with an outer surface 103 of the display panel 102 is described.

The passive terahertz biometric imaging device 100 comprises an image sensor 108 comprising an antenna pixel array 109 arranged to detect terahertz radiation 115, only conceptually shown herein by arrows, produced by the object, for capturing a terahertz image of the object 105.

The antenna pixels, of which one is denoted 110, are configured to detect radiation 115 in a terahertz range. Thus, the antennas are tuned to have higher sensitivity in a specific frequency range than at other frequencies, such that the terahertz radiation produced by the finger can be detected with sufficient sensitivity.

Further, the size of the antennas is such that a large number of antennas are included in the antenna pixel matrix 109. For example, the size of the antenna pixels may be in the range of about 15 micrometers to 150 micrometers, preferably in the range of about 50 micrometers to 100 micrometers.

The image sensor 108 is operative in the frequency range 10 GHz to 100 THz, preferably, 100 GHz to 50 THz, more preferably 300 GHz to 30 THz, more preferably 300 GHz to 10 THz. Thus, the antennas in the antenna pixel array are tuned to efficiently couple to terahertz radiation in the preferred frequency range.

With passive terahertz biometric imaging devices as discloses herein, extracted multispectral biometric images, may provide improved in-depth resolution of the biometric images due to the penetration of terahertz radiation into the human skin, without the need for a dedicated terahertz radiation source. The penetration may be about 0.1 mm to 0.4 mm. In this way, sub-dermal information and e.g. information on sweat duct's physiology may be provided and used for biometric authentication.

The image sensor 108 is connected to an analog-to-digital converter 120 for sampling and converting the analog signals S originating from the antenna pixels 110 to a digital representation of the fingerprint pattern of the finger 105. Further, the image sensor 108 is connected to, as conceptually illustrated by arrows, suitable column and row control and timing circuitry 122 such as including application specific integrated circuits (ASICs) and field programmable gate arrays (FPGA).

In FIG. 3A, the image sensor 108 is shown vertically separated from the transparent display panel 102. Thus, there is a gap between the display panel 102 and the image sensor 108 where additional component may be placed.

Figure 3B:
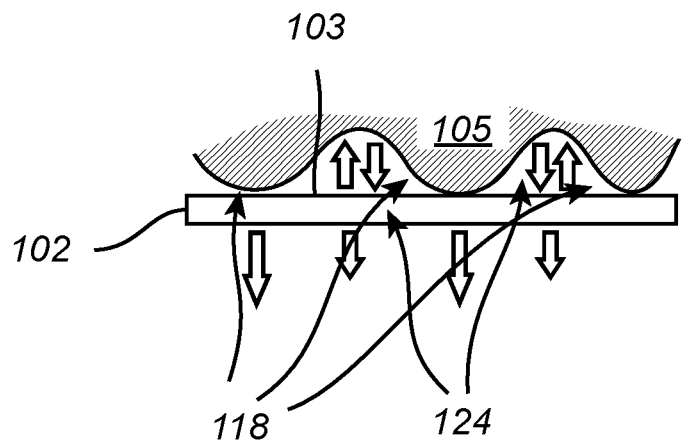
FIG. 3B is a close-up view of FIG. 3A.

The close-up view FIG. 3B illustrates ridges 118 and valleys 124 of a fingerprint in contact with the outer surface 103. The terahertz radiation produced by the finger 105 is modulated by the display panel 102. More specifically, terahertz radiation produced in the valleys 118 is partly reflected back towards the finger 105 due to the refractive index mismatch between the display glass and the air between the valley and the display glass, whereas a larger portion of the terahertz radiation at the ridges 118 being in direct contact with the outer surface 103 is transmitted through the display panel 102. Thereby, the power of the terahertz radiation transmitted from the ridges and that reaches through the display panel 102 is larger than the power of the terahertz radiation transmitted from the valleys and that reaches through the display panel 102.

Figure 4:
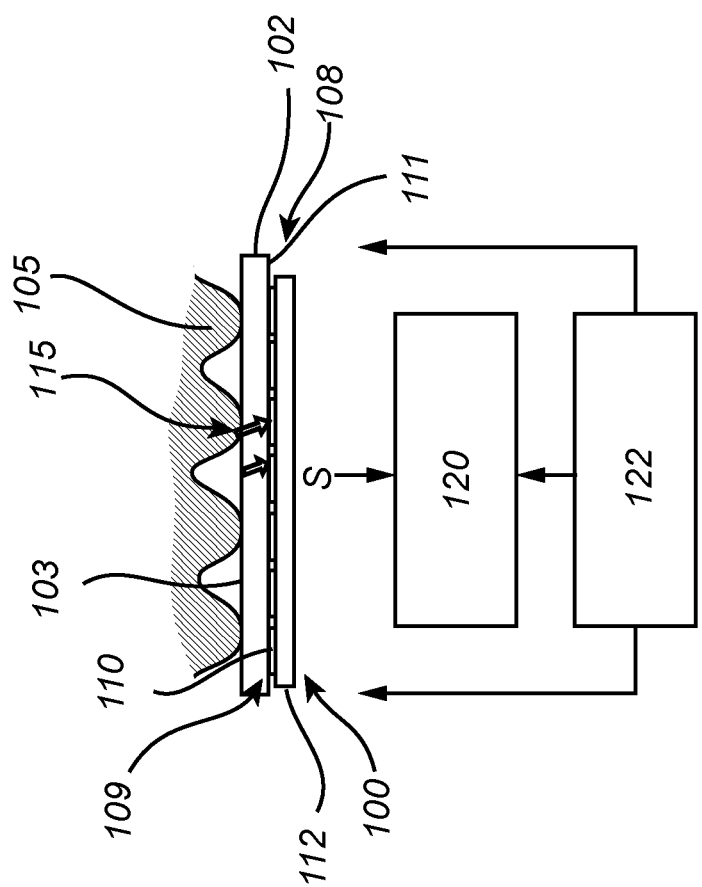
FIG. 4 schematically illustrates a passive terahertz biometric imaging device according to an embodiment of the invention.

In other embodiments, now turning to FIG. 4, the image sensor 108 is attached to the display panel 102. Here, the array 109 of antenna pixels is parallel with the back surface 111 of the display panel, thus, the image sensor 108 is parallel with the general shape of the display panel 102. With this embodiment, the antenna pixels 110 come close to the finger 105 that is to be imaged. The antenna pixels 110 of such image sensor advantageously comprises graphene or another two-dimensional material that can be made flexible to better conform with the shape of the display panel 102. Further, in such embodiments, the substrate 112 carrying the array 109 of antenna pixels advantageously is flexible.

For the antenna pixels 110 to come even close to the finger 105, the image sensor may be laminated directly on the display panel, i.e. on a back side 111 of the display panel 102 opposite the outer surface 103.

Figure 5:
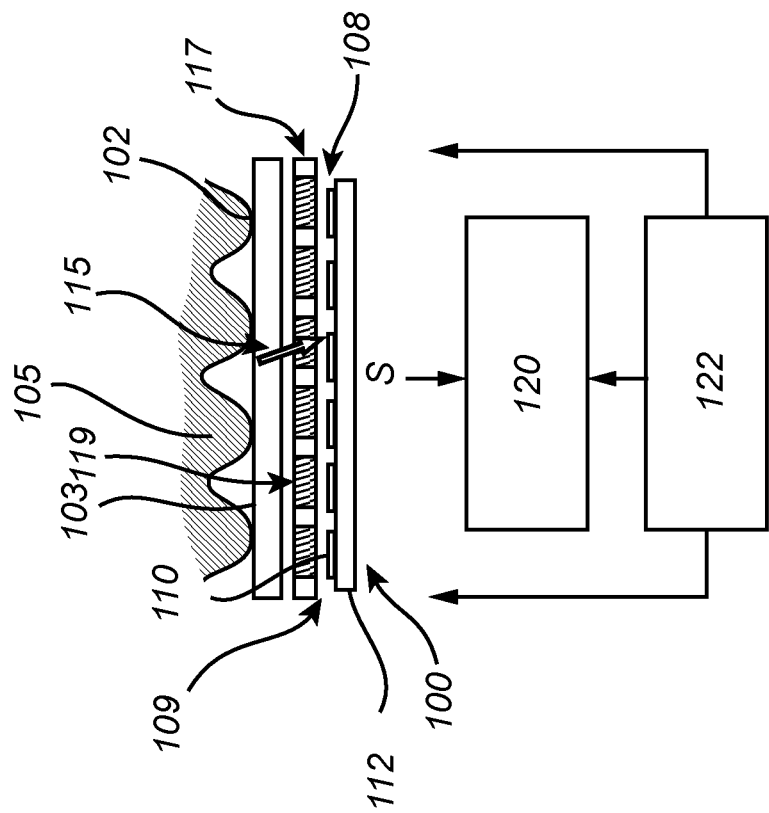
FIG. 5 schematically illustrates a passive terahertz biometric imaging device according to an embodiment of the invention.

FIG. 5 conceptually illustrates a further possible implementation of embodiments of the invention. In this embodiment, the image sensor 108 is located under a display element 117 comprising an array of color controllable pixels 119. In other words, the image sensor 108 and the transparent display panel, here provided as a cover glass 102, are arranged on opposite sides of the display element 117. Various types of display elements can be used in accordance with embodiments. For example, display element based on OLED, u-LED with any type of tri-stimulus emission like RGB, CMY or others.

The image sensor 108 may be laminated on the display element 117, thereby providing for a low stack-up of the biometric imaging device under the display panel 102. The display element 117 may serve as a substrate for the image sensor 108, which may be at least partly transparent.

FIG. 6A conceptually illustrates a further embodiment of the invention in which the image sensor 108 is arranged interleaved between the transparent display panel 102 and a display element 117 comprising an array of color controllable light emitting units 119. Thus, the image sensor 108 is stacked between the color controllable array of light sources 119, e.g. display pixels, and the top cover glass 102. This is especially suitable when the antenna pixels comprise two-dimensional material.

In this embodiment, presented in FIG. 6A, the image sensor 108 is preferably at least partly transparent so that the display pixels 119 are visible to a user from above the transparent display panel 102. This may be achieved by manufacturing the antenna pixels 110 from a two-dimensional material such as graphene, and the substrate from a transparent polymer material.

The antenna pixel array 109 arranged on the substrate 113 as shown in FIG. 6A may be laminated directly on the display element 117. Alternatively, the antenna pixel array 109 arranged on the substrate 112 may be laminated directly on the back side 111 of the display panel 102. These embodiments both provide for low stack-up height.

FIG. 6B illustrates a further possible embodiment of the present invention. Here the image sensor 108 is arranged on the back side 111 of the display panel 102. The display panel 102 here serves as a substrate for the array 109 of antenna pixels 110. Thus, the array 109 of antenna pixels 110 may be manufactured directly on the display panel 102, e.g. provided as a cover glass. It is also possible that the array 109 of antenna pixels 110 are manufactured elsewhere and subsequently transferred to the cover glass.

The array 109 of antenna pixels 110 is interleaved between the display element 117 and the cover glass 102. Preferably, the array 109 of antenna pixels 110 is made from a 2D-material in this embodiment which makes it convenient to manufacture the array 109 of antenna pixels 110 directly on the cover glass 102. Other metal layers and dielectric materials needed for the array 109 of antenna pixels 110 may be deposited directly on the cover glass 102.

Figure 7:
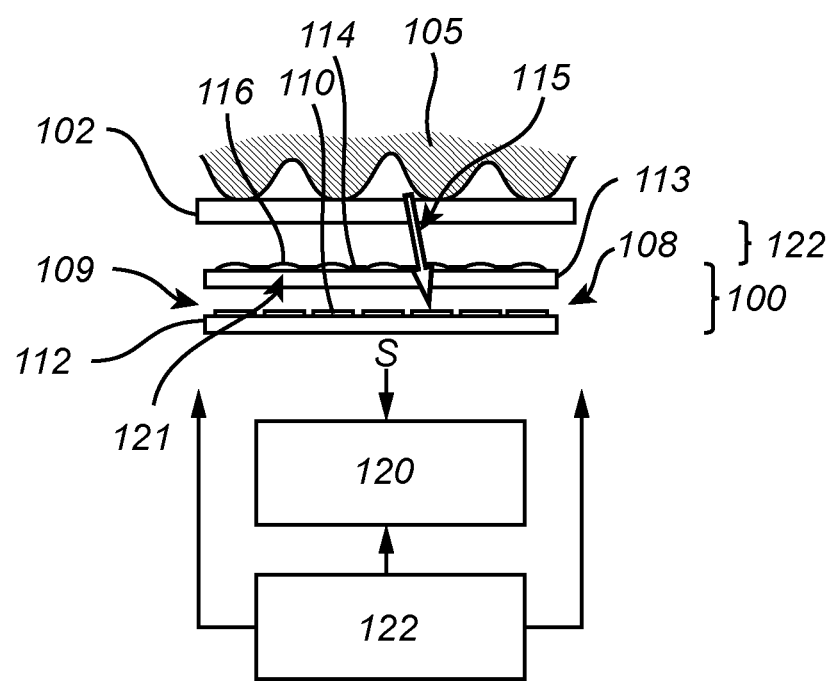
FIG. 7 schematically illustrates a passive terahertz biometric imaging device according to an embodiment of the invention.

Turning now to FIG. 7 which conceptually illustrates a further embodiment of the present invention. The biometric imaging device 100 comprises a transparent substrate 113 arranged to cover the image sensor 108. On the transparent substrate 113 there is arranged an array of terahertz radiation redirecting elements 116 arranged between the display panel 102 and the image sensor 108. Each terahertz radiation redirecting element 116 is configured to redirect terahertz radiation onto the antenna pixel array 109.

In the presently described embodiment, the array of terahertz radiation redirecting elements is an array of microlenses 116, wherein each microlens is configured to redirect terahertz radiation onto a subarray of antenna pixels or to a single antenna pixel in the antenna pixel array.

The microlenses 116 are arranged on a transparent substrate 113 which may optionally comprise an opaque layer 114 covering an upper surface of the transparent substrate 113. The opaque layer 114 further comprises a plurality of separate openings 121 arranged at a distance from each other. The microlenses 116 are each arranged in a respective opening 121 of the optional opaque layer 114 and in the same plane as the opaque layer 114. Moreover, the microlens 116 has the same size and shape as the opening 121 to prevent any stray terahertz radiation which has not passed through the microlens 116 from reaching the image sensor 108.

Each microlens 116 is configured to redirect terahertz radiation through the transparent substrate 113 and onto a subarray of antenna pixels or onto a single antenna pixel 110 in the antenna pixel array 109. The subarrays are defined as arrays of antenna pixels which receive radiation from only one microlens 116. It should further be noted that the microlenses and antenna pixels are not drawn to scale.

The microlens 116 is shown to receive terahertz radiation produced by the finger 105 which has propagated through the display panel 102 before reaching the microlens 116 and the terahertz radiation received by the microlens 116 is focused onto the image sensor 108. In this example embodiment one microlens redirects terahertz radiation to one antenna pixel although it is also conceivable that each microlens redirects radiation to a subarray of antenna pixels. The subarrays or antenna pixels receiving terahertz radiation from the microlenses 116 are preferably non-overlapping with adjacent subarrays receiving terahertz radiation from neighboring microlenses.

The terahertz biometric imaging device 100 may further comprises at least one intermediate layer 122 located between the opaque layer 114 and the display panel 102. The intermediate layer comprises an air gap between the transparent display panel 102 and the lenses 116. Furthermore, the intermediate layer 122 may also comprise an antireflection coating, an optical filter and/or a polarizing filter, which are not illustrated separately herein. It is in general preferable that the refractive index of the microlens 116 is as high as possible and that it is different from the refractive index of any adjacent material above or below the microlens 116.

In some possible implementations the array of microlenses may be replaced by array of vertical waveguides wherein each vertical waveguide is configured to redirect terahertz radiation onto a pixel in the antenna pixel array. A vertical waveguide may be an analogue to an optical collimator, but operative in the terahertz range of radiation.

Figure 8:
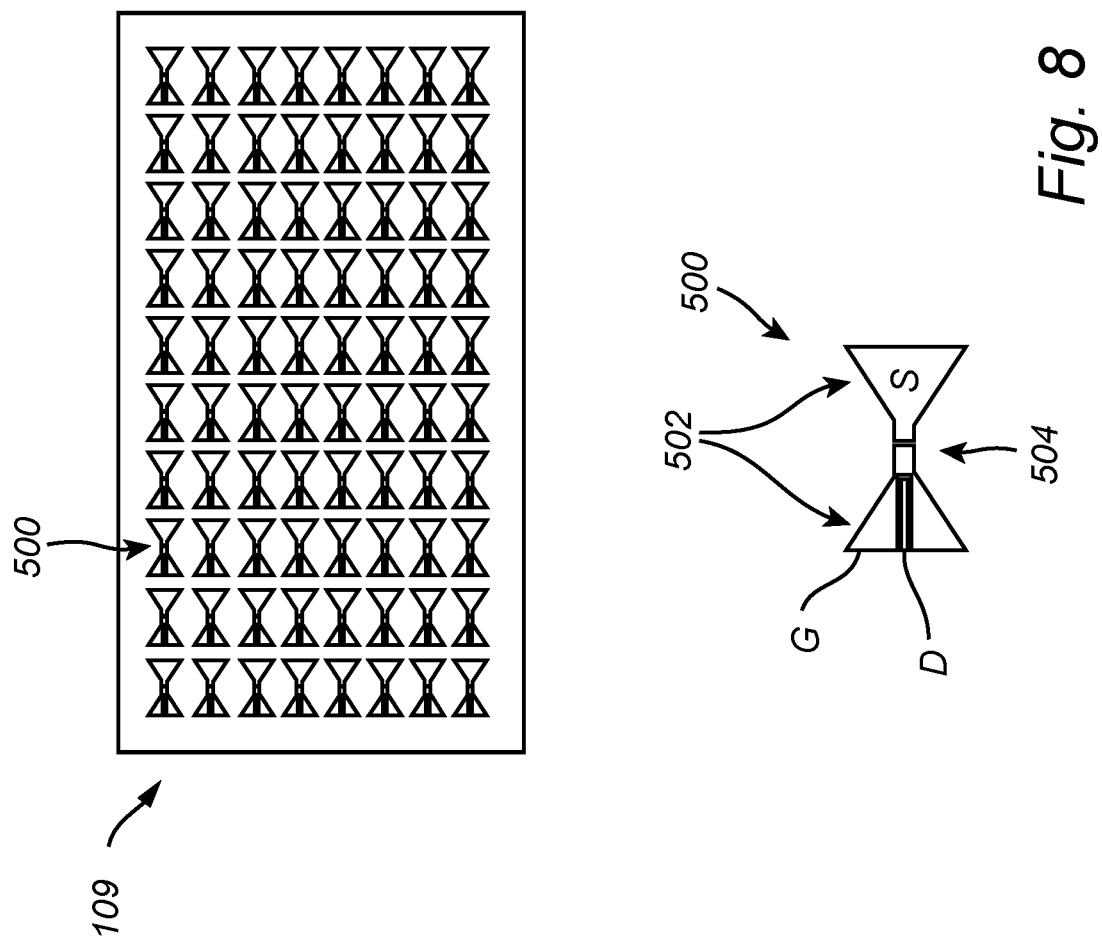
FIG. 8 conceptually illustrates an antenna pixel array and an individual antenna pixel according to an embodiment of the invention.

FIG. 8 conceptually illustrates an example antenna pixel array 109. Each antenna pixel 500 includes an antenna structure 502 and a transistor 504. The antenna structure 502 may be the gate G and source S of the transistor 504. In this specific schematic example embodiment, the antenna pixel 500 is a dipole antenna sensor. The transistor 504 may be made by e.g. standard semiconductor Si, InP, InAsP, GaN transistors or similar. In one advantageous embodiment, the antenna structure 502 and the detector transistor 504 are made in a two-dimensional material, in a single layer. For example, the two-dimensional material may be graphene. The transistor 504 may be a graphene field effect transistor (GFET).

The antenna pixel array 109 in this embodiment may be manufactured using standard thin film technology such as e.g. chemical vapor deposition for graphene, or sputtering, pulsed laser deposition, physical vapor deposition, e-beam lithography or photolithography, etching, etc.

The transistor and antenna together serve to detect, by the antenna, and convert, by the transistor, a detected terahertz radiation impinging on the antennas to a signal at a lower frequency than the frequency of the terahertz radiation. Advantageously, the antenna structure 502 and the transistor 504 are integrated in a single component.

The antenna pixel 500 is configured as a power detector adapted to detect the terahertz radiation and output a DC or low frequency signal related to the power of the incoming terahertz radiation. The transistor serves as a rectifying element of the power detector. In other words, the antennas, i.e. the gate and the source, are configured to receive the terahertz radiation, and the transistor is configured to convert and rectify the received signal to a DC or low frequency signal. The DC or low frequency signal may be read by an ADC.

The antenna structure 502 and the transistor structure 504 may be made in a single layer, thereby providing an antenna pixel array 109 that is relatively simple to manufacture. The antenna pixel 500 may be a planar antenna, thereby providing an image sensor that advantageously barely contributes to the stack-up of the biometric imaging sensor, thus providing a thin image sensor.

Figure 9:
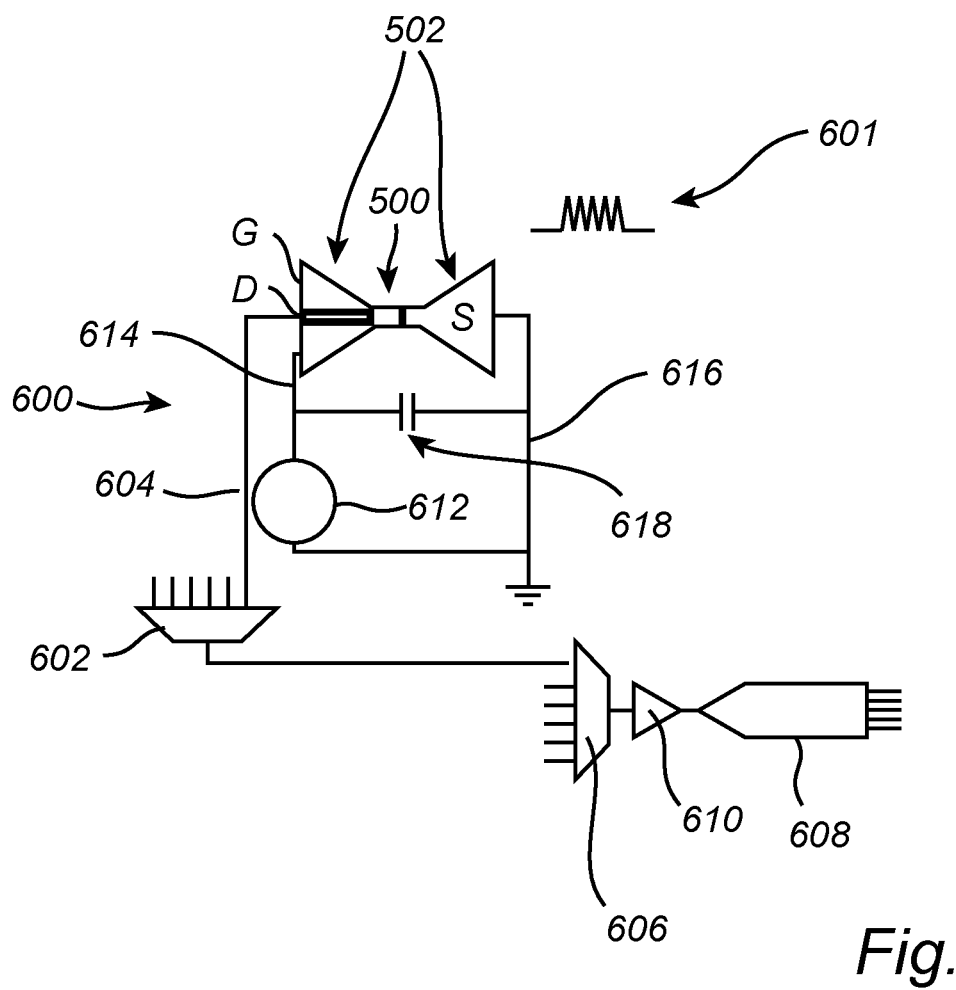
FIG. 9 conceptually illustrates a sensing circuitry for the provision of a sensing signal from an antenna in the antenna pixel array.

Turning to FIG. 9 which illustrates an example read-out circuit 600 for a power detector 500 configured to detect incoming terahertz radiation 601. The drain electrode D is connected to a multiplexer 602 via a read-out line 604, and a further multiplexer 606 may be connected in series with the first multiplexer 602 in order to handle signals from the rows and columns of power detectors in the array 109. The signals from the power detector 500 are low frequency or DC signals. The output of the multiplexer 606 is connected to an analog-to-digital converter 608 in series for sampling and converting the analog signals originating from the power detector 500 to a digital representation of e.g. the fingerprint pattern of a finger 104. In some implementations, an amplifier circuit 610 is inserted between the second multiplexer 606 and the ADC 608, although this is not strictly required.

A direct current source 612 is connected through lines 614 and 616 to the gate G and source S, respectively. The DC source 612 is arranged to feed the power detector 500 with a DC voltage. The gate G, and the source S, are connected through the capacitor 618, effectively providing a diode-connected transistor at high frequencies, i.e. the gate G and the source S are electrically shorted through the capacitor 618 at sufficiently high frequencies, as tailored by the capacitor, preferably at frequencies exceeding the lower range of the terahertz frequencies desirable to detect for imaging.

Generally, the incoming terahertz radiation is detected through half-wave rectification and low-pass filtering. More specifically, when radiation 601 impinges on the gate G and the source S serving as antennas 502 of the power detector 500, the electrical potential of the gate G and the source S is modulated at the frequency of the incoming terahertz radiation 601, whereby the DC voltage feed is passed to the drain D. However, due to the diode-tied transistor configuration, the output at the drain D, is a half-wave rectified signal. This half-wave rectified signal is filtered through e.g. capacitors and/or inductive components such as coils, to thereby provide a DC or low-frequency sensing signal to the multiplexor 602. For example, a capacitor may be inserted in parallel across the drain D, and ground, and/or inductive components may be connected in series with the drain D of the power detector 500. Accordingly, the power detector 500 operates as a rectifying transistor and as an antenna.

Figure 10:
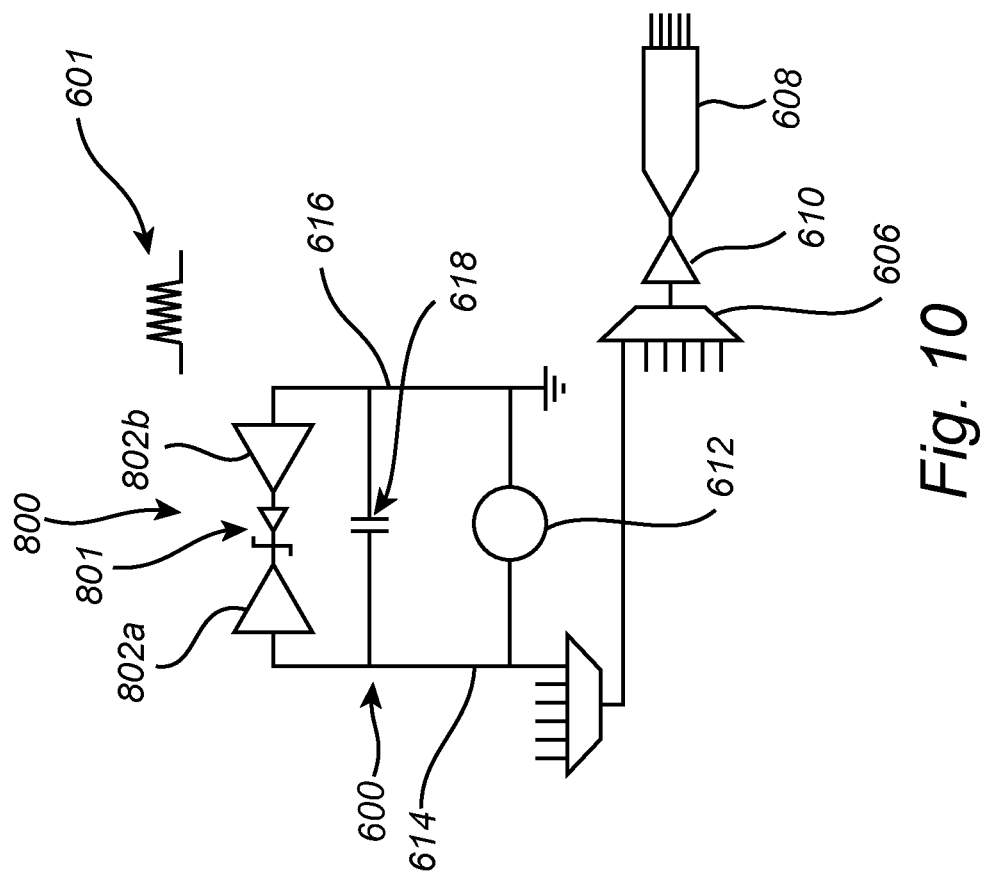
FIG. 10 conceptually illustrates a sensing circuitry for the provision of a sensing signal from an antenna in the antenna pixel array.

FIG. 10 illustrates another possible implementation of the inventive concept in which a power detector 800 in the form of a dipole antenna sensor with a rectifying diode 801 connected between the receiver antennas 802a-b. The read-out circuit 600 is in this implementation the same as the one described with reference to FIG. 8.

Generally, an antenna pixel may comprise one or several high on chip frequency devices such as transistor, transistors, diode or diodes.

Accordingly, a power detector may comprise at least one on-chip transistor structure, connected to the antenna structure of the antenna pixel, or at least one on-chip diode connected to the antenna structure of the pixel.

Figure 11:
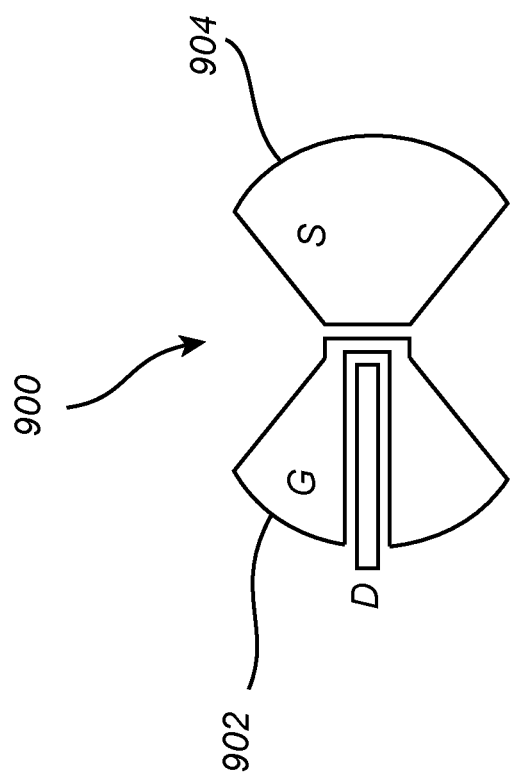
FIG. 11 conceptually illustrates an example antenna pixel according to an embodiment of the invention.

FIG. 11 conceptually illustrates an example antenna pixel 900, e.g. a power detector of bow tie configuration. The power detector 900 comprises a gate G, a source S, and a drain D. The geometry of the gate G and source S at least partly determines the resonance frequency that the power detector is tuned at. More precisely, the resonance frequency of the power detector, is defined by the electrical coupling between the drain D and source S and gate G, and the geometry of the various parts of the power detector. Preferably, the operative frequency range of the antenna pixel is included in the range of 10 GHz to 100 THz, preferably 100 GHz to 50 THz, more preferably 300 GHz to 30 THz.

Here, the gate G and source S of the bow-tie power detector 900 each comprises a curved distal edge 902 and 904, respectively. In other words, the gate G and source S each comprise one end that is shaped with a predetermined radius of curvature as seen from above. The shape of the distal ends 902 and 904 may be adapted for tuning the operation frequency of the power detector 900. Further, the at least partly circular geometry provided by the curved distal ends 902, 904 advantageously provides a more polarization independent antenna compared to dipole antennas employing more straight geometries.

In preferred embodiments, the antenna pixels, e.g. the power detectors, are made from a two-dimensional material, such as graphene. This advantageously enables for manufacturing of the power detector on a flexible substrate without compromising the operation of the power detector significantly. The flexible substrate may comprise of e.g. PET (Polyethylene terephthalate), PEN (Polyethylene naphthalate), or any other similar materials. This image sensor provides for integration under displays of almost arbitrary shapes, e.g. under a curved display panel, whereby the flexible image sensor may be conformally shaped with the curved display panel. Further, using graphene provides for a transistor with improved performance compared to conventional 3D transistors.

Figure 12:
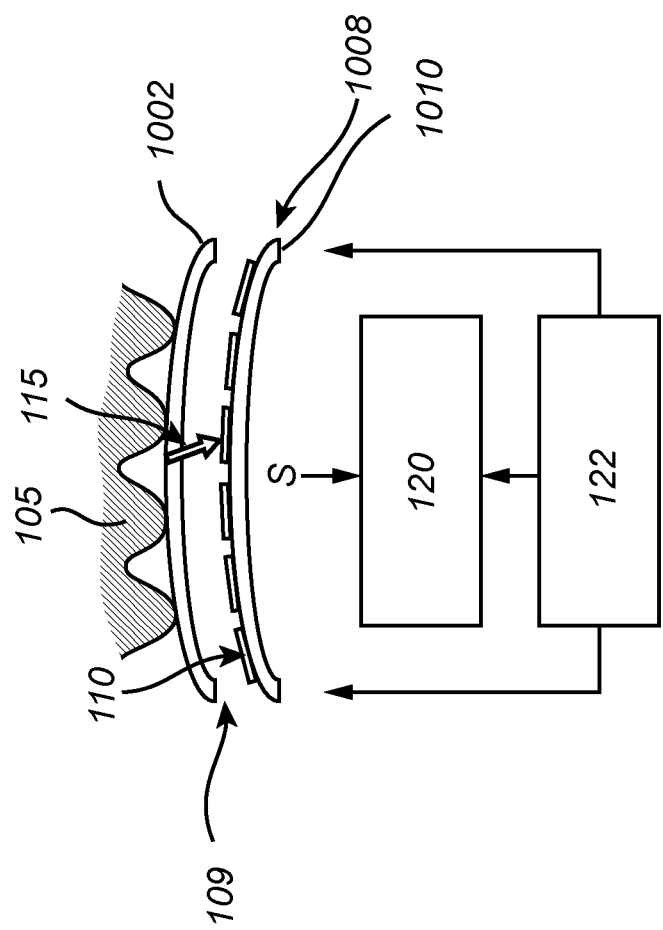
FIG. 12 schematically illustrates a passive terahertz biometric imaging device arranged under a curved display panel according to a further embodiment of the invention.

With regards to the above, and now turning to FIG. 12, the passive terahertz biometric imaging device 1008 may be configured to be arranged under an at least partially transparent and curved display panel 1002 and configured to capture an image of an object 105 located on an opposite side of the at least partly transparent curved display panel 1002. The image sensor 1008 comprises an antenna pixel array 109 and a flexible substrate 1010 that is conformally shaped with the curvature of the transparent curved display panel 1002.

FIG. 13 is a flow-chart of method steps for manufacturing an image sensor for a terahertz biometric imaging device according to embodiments of the invention. The method comprises step S102 of providing a cover glass 102 configured to cover a display for an electronic device. Subsequently, providing S104 a layer of a two-dimensional material 1400 on the cover glass 102. Next, patterning S106 the layer of two-dimensional material 1400 to form an array of antenna pixels 110 configured to detect terahertz radiation.

The two-dimensional material may be deposited directly on the cover glass or the two-dimensional material may be transferred from a substrate onto the cover glass. Other materials needed for the antenna pixels such as metal lines and dielectric materials may be deposited directly on the cover glass using known microfabrication techniques. The two-dimensional material may be graphene, although other two-dimensional materials are also conceivable, such as e.g. silicene, germanene, and phosphorene but also TMDs as i.e., MoS2, WSe2, etc.

Electrical connections to the antenna pixels for providing the sensing signals (S) to the read-out circuitry may be formed from two-dimensional metal lines on the sides of the cover glass and through e.g. metal pads and/or conductive adhesives. Such two-dimensional metal lines are advantageously not visible to the human eye.

A control unit may include a microprocessor, microcontroller, programmable digital signal processor or another programmable device. The control unit may also, or instead, include an application specific integrated circuit, a programmable gate array or programmable array logic, a programmable logic device, or a digital signal processor. Where the control unit includes a programmable device such as the microprocessor, microcontroller or programmable digital signal processor mentioned above, the processor may further include computer executable code that controls operation of the programmable device. It should be understood that all or some parts of the functionality provided by means of the control unit (or generally discussed as "processing circuitry") may be at least partly integrated with the biometric imaging device.

Even though the invention has been described with reference to specific exemplifying embodiments thereof, many different alterations, modifications and the like will become apparent for those skilled in the art. Also, it should be noted that parts of the imaging device and method for manufacturing the imaging device may be omitted, interchanged or arranged in various ways, the imaging device yet being able to perform the functionality of the present invention.

The microlenses are herein illustrated as plano-convex lenses having the flat surface orientated towards the transparent substrate. It is also possible to use other lens configurations and shapes. A plano-convex lens may for example be arranged with the flat surface towards the display panel, and in one embodiment the lens may be attached to a bottom surface of the display panel even though the imaging performance may be degraded compared to the reverse orientation of the microlens. It is also possible to use other types of lenses such as convex lenses. An advantage of using a plano-convex lens is the ease of manufacturing and assembly provided by a lens having a flat surface.

Note also that the size of components in the drawings are selected for clarity and are not necessarily to scale, as understood by the skilled person. The microlenses may be arranged in an array having a pitch in the range of 50 µm to 2 mm.

The microlenses may be circular lenses having a diameter in the range of 20 µm to 1 mm.

The microlenses may be rectangular lenses having a length of a shortest side in the range of 20 µm to 1 mm.

Moreover, the microlens may have a height in the range of 2 µm to 600 µm.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. A passive terahertz biometric imaging device operative in the terahertz range of radiation and configured to be arranged under an at least partially transparent display panel and configured to capture a terahertz image of a biometric object located on an opposite side of the transparent display panel, the terahertz biometric imaging device comprising:
    an image sensor comprising an antenna pixel array configured to detect radiation in a terahertz range and arranged to detect terahertz radiation produced by the biometric object, for capturing a terahertz image of the biometric object without assisting terahertz radiation that illuminates the biometric object, wherein subdermal layers of the biometric object are detectable in the captured terahertz image,
    wherein each of the pixels comprises a power detector including an antenna structure configured to sense terahertz radiation produced by the biometric object, and at least one on-chip frequency converting element connected to the antenna structure and configured to convert the sensed terahertz radiation to a signal at a lower frequency than the frequency of the terahertz radiation, or to a DC signal, for an analogue-to-digital converter to read as input.

2. The passive terahertz biometric imaging device according to claim 1, wherein the image sensor is attached to the display panel.

3. The passive terahertz biometric imaging device according to claim 1, wherein the image sensor comprises a substrate supporting the antenna pixel array.

4. The passive terahertz biometric imaging device according to claim 3, wherein the substrate is made from a flexible material.

5. The passive terahertz biometric imaging device according to claim 1, wherein the image sensor is laminated directly on the display panel.

6. The passive terahertz biometric imaging device according to claim 1, wherein the image sensor is at least partly transparent.

7. The passive terahertz biometric imaging device according to claim 1, where the image sensor is stacked between a display element comprising an array of color controllable light sources and a cover glass of the display panel.

8. The terahertz biometric imaging arrangement according to claim 1, wherein the array of antenna pixels is manufactured on the display panel.

9. The passive terahertz biometric imaging device according to claim 1, wherein the image sensor is arranged under a display element comprising an array of color controllable light sources.

10. The passive terahertz biometric imaging device according to claim 9, wherein the image sensor is laminated on the display element.

11. The passive terahertz biometric imaging device according to claim 1, comprising:
    an array of terahertz radiation redirecting elements arranged between the display panel and the image sensor, wherein each terahertz radiation redirecting element is configured to redirect terahertz radiation onto the antenna pixel array.

12. The terahertz biometric imaging device according to claim 1, wherein the frequency converting element comprises at least one on-chip transistor structure, connected to the antenna structure of the antenna pixel, or at least one on-chip diode connected to the antenna structure of the pixel.

13. The terahertz biometric imaging arrangement according to claim 1, wherein a transistor structure and the antenna structure are made in a single component.

14. The passive terahertz biometric imaging device according to claim 12, wherein a level of a DC voltage output from an antenna pixel is based on the power of the detected terahertz radiation.

15. The passive terahertz biometric imaging device according to claim 1, wherein the antenna pixels are made from an at least partly transparent material.

16. The passive terahertz biometric imaging device according to claim 1, wherein the antenna pixel array comprises a two-dimensional material.

17. The passive terahertz biometric imaging device according to claim 1, wherein the antenna pixel array comprises graphene.

18. The passive terahertz biometric imaging device according to claim 1, wherein the image sensor is operative to detect terahertz radiation in a frequency range excluding the range of visible light.

19. An electronic device comprising:
    an at least partly transparent display panel;
    the passive terahertz biometric imaging arrangement according to claim 1, and processing circuitry configured to:
        receive a signal from the passive terahertz biometric imaging arrangement indicative of a biometric object touching the at least partly transparent display panel,
        perform a biometric authentication procedure based on the detected biometric object.

20. A method of manufacturing the image sensor for the passive terahertz biometric imaging device of claim 1, the method comprising:
    providing a cover glass configured to cover a display for an electronic device;
    providing a layer of a two-dimensional material on the cover glass;
    patterning the layer of two-dimensional material to form the antenna pixel array configured to detect terahertz radiation.

* * * * *